(12) United States Patent
Young et al.

(10) Patent No.: US 10,094,744 B2
(45) Date of Patent: *Oct. 9, 2018

(54) COLLECTION DEVICE AND MATERIAL

(71) Applicant: PURITAN MEDICAL PRODUCTS COMPANY, LLC, Guilford, ME (US)

(72) Inventors: Terry Young, Guilford, ME (US); Timothy Templet, Guilford, ME (US); Paul Dube, Guilford, ME (US); Todd Dixon, Guilford, ME (US); Armand F. Lewis, Mattapoisett, MA (US); Yong K. Kim, Dartmouth, MA (US)

(73) Assignee: PURITAN MEDICAL PRODUCTS COMPANY, LLC, Guilford, ME (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/969,536

(22) Filed: Dec. 15, 2015

(65) Prior Publication Data

US 2016/0097700 A1    Apr. 7, 2016

Related U.S. Application Data

(63) Continuation of application No. 13/798,497, filed on Mar. 13, 2013, now Pat. No. 9,274,029, which is a
(Continued)

(51) Int. Cl.
*G01N 1/04* (2006.01)
*A61B 10/00* (2006.01)
(Continued)

(52) U.S. Cl.
CPC ............ *G01N 1/04* (2013.01); *A61B 10/0045* (2013.01); *B32B 37/16* (2013.01); *D01D 5/36* (2013.01);
(Continued)

(58) Field of Classification Search
CPC .......... C12M 1/261; C12M 1/26; C12M 1/30; B01L 2300/0838; A61B 10/0096
(Continued)

(56) References Cited

U.S. PATENT DOCUMENTS 3,163,160 A    12/1964  Cohen
3,900,651 A    8/1975   Hoppe et al.
(Continued)

FOREIGN PATENT DOCUMENTS

EP    0223745       5/1987
EP    0244156 B1    4/1990
(Continued)

OTHER PUBLICATIONS

Page 1179 of the American Heritage Dictionary, Second College Edition (1985, Houghton Mifflin Company, Boston, MA). (Year: 1985).*

(Continued)

*Primary Examiner* — Michael L Hobbs
(74) *Attorney, Agent, or Firm* — Nixon & Vanderhye P.C.

(57) ABSTRACT

Swabs, materials and methods of making same, include randomly arranged sea-island bicomponent fibers. According to certain embodiments, swabs and methods of using such swabs are provided so as to collect and release a biological sample comprising a flock fiber tipped applicator wherein the flock fibers are sea-island bicomponent fibers attached to an end portion of the applicator with an adhesive selected from the group consisting of a photocurable acrylic adhesive and a polyurethane adhesive, the bicomponent fibers being structurally stable in water and the sea component of the bicomponent flock fibers being intact.

18 Claims, 2 Drawing Sheets

Related U.S. Application Data continuation of application No. 12/849,250, filed on Aug. 3, 2010, now Pat. No. 8,420,385.

(60) Provisional application No. 61/326,466, filed on Apr. 21, 2010.

(51) Int. Cl.
| | |
|---|---|
| *D01D 5/36* | (2006.01) |
| *D01F 8/12* | (2006.01) |
| *D01F 8/14* | (2006.01) |
| *B32B 37/16* | (2006.01) |
| *G01N 1/10* | (2006.01) |
| *A61B 10/02* | (2006.01) |
| *G01N 1/02* | (2006.01) |

(52) U.S. Cl.
CPC ............... *D01F 8/12* (2013.01); *D01F 8/14* (2013.01); *G01N 1/10* (2013.01); *A61B 10/007* (2013.01); *A61B 10/0051* (2013.01); *A61B 2010/0067* (2013.01); *A61B 2010/0074* (2013.01); *A61B 2010/0216* (2013.01); *G01N 2001/028* (2013.01); *Y10T 156/10* (2015.01); *Y10T 156/1043* (2015.01); *Y10T 156/1089* (2015.01)

(58) Field of Classification Search
USPC .................. 435/29, 309.1; 156/60; 604/1
See application file for complete search history.

(56) References Cited

U.S. PATENT DOCUMENTS

| | | | |
|---|---|---|---|
| 4,030,978 | A | 6/1977 | Abramson |
| 4,039,934 | A | 8/1977 | Ostashko |
| 4,059,404 | A | 11/1977 | Schuster et al. |
| 4,101,525 | A | 7/1978 | Davis et al. |
| 4,421,809 | A | 12/1983 | Bish |
| 4,519,804 | A | 5/1985 | Kato et al. |
| 4,707,450 | A | 11/1987 | Nason |
| 4,719,181 | A | 1/1988 | Schobel |
| 4,749,655 | A | 6/1988 | Corasaniti |
| 4,767,398 | A | 8/1988 | Blasius, Jr. |
| 4,820,259 | A | 4/1989 | Stevens |
| 4,861,343 | A | 8/1989 | Neunzig |
| 4,877,037 | A | 10/1989 | Ko |
| 5,009,846 | A | 4/1991 | Gavet |
| 5,163,441 | A | 11/1992 | Monthony |
| 5,623,941 | A | 4/1997 | Hedberg |
| 5,738,643 | A | 4/1998 | Stedic |
| 5,762,494 | A | 6/1998 | Archambault |
| 5,944,519 | A | 8/1999 | Griffiths |
| 6,211,309 | B1 | 4/2001 | McIntosh et al. |
| 6,232,567 | B1 | 6/2001 | Bonino |
| 6,352,513 | B1 | 3/2002 | Anderson |
| 6,450,810 | B1 | 9/2002 | Fischer |
| 6,835,865 | B2 | 12/2004 | Quincy, III |
| 6,838,172 | B2 | 1/2005 | Yoon et al. |
| 7,022,289 | B1 | 4/2006 | Schlein |
| 7,622,188 | B2 | 11/2009 | Kamiyama et al. |
| 8,114,027 | B2 | 2/2012 | Triva |
| 8,420,385 | B2 | 4/2013 | Young et al. |
| 2002/0001539 | A1 | 1/2002 | DiCesare et al. |
| 2002/0197738 | A1 | 12/2002 | Matsumoto et al. |
| 2003/0073932 | A1 | 4/2003 | Varey |
| 2003/0108846 | A1 | 6/2003 | Hoertsch |
| 2003/0120180 | A1 | 6/2003 | Kaylor et al. |
| 2003/0203695 | A1 | 10/2003 | Polanco et al. |
| 2004/0014063 | A1 | 1/2004 | Batteux |
| 2004/0158188 | A1 | 8/2004 | Kauffmann |
| 2004/0197730 | A1 | 10/2004 | Rowe |
| 2005/0181517 | A1 | 8/2005 | Chandler et al. |
| 2006/0115805 | A1 | 6/2006 | Hansen et al. |
| 2006/0142668 | A1 | 6/2006 | Triva |
| 2007/0208274 | A1 | 9/2007 | Ostrowski et al. |
| 2007/0259177 | A1 | 11/2007 | Gupta et al. |
| 2007/0264520 | A1 | 11/2007 | Wood et al. |
| 2007/0282223 | A1 | 12/2007 | Larkin |
| 2008/0125687 | A1 | 5/2008 | Flick et al. |
| 2008/0208100 | A1 | 8/2008 | Wolff |
| 2009/0030341 | A1 | 1/2009 | Kshirsagar et al. |
| 2010/0029158 | A1 | 2/2010 | Kamiyama et al. |
| 2010/0068516 | A1 | 3/2010 | Yoon et al. |
| 2010/0075143 | A1 | 3/2010 | Hashimoto et al. |
| 2010/0274155 | A1 | 10/2010 | Battrell et al. |
| 2011/0028861 | A1 | 2/2011 | Triva |
| 2011/0262951 | A1 | 10/2011 | Young et al. |
| 2013/0196363 | A1 | 8/2013 | Young et al. |

FOREIGN PATENT DOCUMENTS

| | | | |
|---|---|---|---|
| EP | 0 643 131 | A2 | 3/1995 |
| EP | 0707836 | A2 | 4/1996 |
| JP | 3-176046 | | 7/1991 |
| JP | 11-152643 | | 6/1999 |
| JP | 2004-130209 | | 4/2004 |
| JP | 2005-513513 | | 5/2005 |
| JP | 2008-107332 | | 5/2008 |
| JP | 2008-122372 | | 5/2008 |
| JP | 2009-36781 | | 2/2009 |
| JP | 2009-139226 | | 6/2009 |
| WO | WO89/10724 | | 11/1989 |
| WO | WO9212863 | | 8/1992 |
| WO | WO0054024 | | 9/2000 |
| WO | WO 02/42528 | A1 | 5/2002 |
| WO | WO 02/42529 | A1 | 5/2002 |
| WO | WO 02/088438 | A1 | 11/2002 |
| WO | WO 2004/086979 | A1 | 10/2004 |
| WO | WO2004/086979 | A1 | 10/2004 |
| WO | WO2004086979 | | 10/2004 |
| WO | WO-2005013759 | A1 * | 2/2005 ............. A45D 19/02 |
| WO | WO-2005110316 | A1 * | 11/2005 ............. A61F 13/38 |
| WO | WO2007/075412 | A2 | 7/2007 |
| WO | WO2007/075412 | A3 | 7/2007 |
| WO | WO2008/131033 | A1 | 10/2008 |
| WO | WO 2009/018473 | A1 | 2/2009 |
| WO | WO2009/018607 | A1 | 2/2009 |
| WO | WO2009/134509 | A2 | 11/2009 |
| WO | WO2009/136892 | A1 | 11/2009 |
| WO | WO2009/140356 | A1 | 11/2009 |

OTHER PUBLICATIONS

Grafe et al, "Polymeric Nanofibers and Nanofiber Webs: A New Class of Nonwovens", INTC 2002: International Nonwovens Technical Conference (Joint INDA—TAPPI Conference), Atlanta, Georgia, Sep. 24-26, 2002 (13 pages).

Ndaro et al., "Splitting of Islands-in-the-Sea Fibers (PA6/COPET) During Hydroentangling of Nonwovens", Journal of Engineered Fibers and Fabrics, vol. 2, Issue 4, 2007.

Fedorova, N., "Investigation of the Utility of Islands-in-the-Sea Bicomponent Fiber Technology in the Spunbond Process" A dissertation submitted to the Graduate Faculty of North Carolina State University, In partial fulfillment of the requirements for the Degree of Doctor of Philosophy, Raleigh, NC 2006.

"Flock and flocking—understanding the process" printed from http://docucomp.archive.org on Jul. 22, 2008 (5 pages).

"Understanding the flocking process" printed from http://web.archive.org on Jul. 22, 2008 (7 pages).

European Search Report dated Jul. 22, 2011, issued in connection with EP 10 25 1388.4.

European Search Report dated Jul. 25, 2011, issued in connection with EP 10 25 1389.2.

International Search Report and Written Opinion dated Jun. 15, 2011, issued in connection with PCT/US2010/002155.

International Search Report and Written Opinion dated Jun. 15, 2011, issued in connection with PCT/US2010/002154.

Sahbaee Bagherzadeh, "Abrasion and Pilling Resistance of Nonwoven Fabrics Made from Bicomponent Fibers", Master dissertation, North Caroline State University, Releigh, NC, USA, 2007.

(56) References Cited

OTHER PUBLICATIONS

Certified English translation of JP 2004-130209 (Apr. 30, 2004) and certification.
U.S. Patent Office File History of U.S. Appl. No. 10/543,873 titled "Swab for Collecting Biological Specimens".
US Patent Office, Office Actions/Communications dated Mar. 4, 2011, Nov. 29, 2010, Jul. 19, 2010, Jul. 15, 2010, Mar. 23, 2010, Dec. 14, 2009, Aug. 14, 2009, Apr. 14, 2008, Mar. 17, 2008, in U.S. Appl. No. 10/543,873, titled "Swab for Collecting Biological Specimens".
Submissions by applicants dated Nov. 30, 2010, Sep. 23, 2010, Aug. 23, 2010, Jun. 8, 2010, Dec. 17, 2009, Nov. 16, 2009, May 27, 2009, May 8, 2007,Jul. 28, 2005 in U.S. Appl. No. 10/543,873, titled "Swab for Collecting Biological Specimens".
GB406850(A) Mislowitzer, (abstract) published Mar. 8, 1934 "Devices for dispatching "Abstriche" Blood Samples and the Like for Bacteriological and Diagnostic Purposes".
Pages 212 and 147 of Merriam Webster's Collegiate Dictionary, Tenth Edition (1994) Merriam-Webster Incorporated.
Declaration of Daniele Triva Under 37 CFR §1.132 dated Nov. 10, 2009, filed in U.S. Appl. No. 10/543,873, bearing USPTO date stamp of Nov. 18, 2009.
Castriclano et al "Increased Rates of respiratory Viral [RV] Infections Using Flocked Swabs and UTM-RT" 17th European Congress of Clinical Microbiology and Infectious Diseases, Munich, Germany, Mar. 31-Apr. 3, 2007 (1 page), as mentioned in Declaration of Daniele Triva Under 37 CFR §1.132 dated Nov. 10, 2009, filed in U.S. Appl. No. 10/543,873, bearing USPTO date stamp of Nov. 18, 2009.
US Patent Office, Office Actions/Communications dated Mar. 4, 2011, Nov. 29, 2010, Aug. 31, 2010, May 22, 2009, Jan. 27, 2009, Oct. 30, 2008, Feb. 28, 2008, Nov. 30, 2007, Aug. 27, 2007, May 31, 2007, in U.S. Appl. No. 10/543,873, titled "Swab for Collecting Biological Specimens", Triva.
Submissions by applicants dated Nov. 30, 2010, May 27, 2009 Sep. 23, 2010, Nov. 10, 2008, Jul. 1, 2008, Mar. 4, 2008, Feb. 25, 2008, Mar. 21, 2008, Aug. 28, 2007, in U.S. Appl. No. 10/543,873, titled "Swab for Collecting Biological Specimens".
JP2004000587 "Applicator Covered With Flocking of Different Kinds of Fibers Especially for Cosmetics or the Like", Published Jan. 8, 2004, Gueret (English Abstract).
JP2003425911(A) "Specimen Collection Appliance Set", Published Dec. 12, 2000, Arai (English Abstract).
JP2002067201(A) "Flocked Material and Decorative Sheet as well as its Manufacturing Method", Published Mar. 5, 2002, Obata (English Abstract).
JP05-027671,U machine translation printed Sep. 21, 2010, publication dated Apr. 9, 1993.
International Preliminary Report on Patentability mailed in PCT/EP2004/003392 completed Feb. 22, 2005 by Tragoustis of European Patent Office.
Abu-Diab et al. "comparison between Pernasal Flocked Swabs and Nasopharyngeal Aspirates for Detection of Common Respiratory Viruses in Samples from Children" Journal of Clinical Microbiology, Jul. 2008, pp. 2414-2417, vol. 46., No. 7.
Fiebelkorn et al "Performance of Rapid EIA, DFA, RMix, and Conventional Culture for Detection of Respiratory Viruses in Pediatric vs. Adult Populations" paper M-35, UT Health Science Center, contained in U.S. Appl. No. 10/543,873, titled "Swab for Collecting Biological Specimens", Triva, Clinical Virology Symposium—CVS 2008, May 5, 2008.
Walsh et al "Comparison of RSV RNA Recovery by PCR Using Different Methods of Specimen Preservation" Kern Medical Center, contained in U.S. Appl. No. 10/543,873, titled "Swab for Collecting Biological Specimens", Triva, American College of Emergency Physicians (ACEP) Scientific Assembly 2007, Washington State Convention Center, Seattle, WA, Oct. 8-11, 2007.
Walsh et al "Comparison of Three Nasal Collection Specimen Methods for the Detection of Pediatric Respiratory Infectious Disease" Medical Diagnostic Laboratories, contained in U.S. Appl. No. 10/543,873, titled "Swab for Collecting Biological Specimens", Triva, Association of Molecular Pathlogy (AMP) 13th Annual Meeting, Nov. 7-10, 2007.
Biggs et al "Prevalence of Pediatric Respiratory Infections in a Suburban Philadelphia Hospital" 23rd Annual Clinical Virology Symposium and Annual Meeting of the Pan American Society, Clearwater Beach, FL, Apr. 30, 2007.
Silbert "Comparative Study of the Ability of a New and Novel Swab transport System to Maintain Viability of Clinically Important Aerobes at Room and Refrigerator Temperatures" C-100, ASM 106th General Convention—Orlando, Florida, May 2006.
Jones "A new concept for transporting clinical material on flocked swabs in liquid amies medium" C-107, ASM 106th General Convention—Orlando, Florida—May 22-24, 2006.
Van Horn et al "Evaluation and Comparison of Three Swab Collection and Transport Systems Tested by the CLSI M40-A Method" C-108, ASM 106th General Convention—Orlando, Florida—May 22-24, 2006.
Sarina et al "Comparative Evaluation of Three Transport Swabs Potential to Maintain Viability of Clinically Important Aerobic and Anaerobic Organisms" C-362, ASM 106th General Convention—Orlando, Florida—May 22-24, 2006.
Condon et al "Comparison of the Copan Transystem Swab and the Copan ESwab for the Preservation and Recovery of Fastidious Bacteria" ASM 2007, Abstract C-363.
Biggs et al "Evaluation of ESwab a New Multipurpose Liquid Swab Transport System for Aerobic and Anaerobic Bacteriology" ASM 2007, Abstract C-365.
Silbert et al "Complete MRSA Nasal Screening Using a Single, New and Novel Swab System" C-368, ASM 107th General Convention—Toronto CA, May 2007.
DeFields et al, "P-19: Evaluation of Flocked Nylon Swabs (Copan ESwab) vs Rayon Fibre Swabs (Copan Venturi Transystem) for Bacterial Culture" contained in U.S. Appl. No. 10/543,873 file history, titled "Swab for Collecting Biological Specimens", Triva, the Canadian Journal of Infectious Diseases & Medical Microbiology, Jan./Feb. 2007, vol. 18, No. 1.
Biggs et al "Benefirs of Using Copan's Universal Transport Medium (UTM) and Flocked Swab with the Binax Now Flu A/B Test System for Reflex Testing", contained in U.S. Appl. No. 10/543,873 file history, titled "Swab for Collecting Biological Specimens", Triva, 23rd Annual Clinical Virology Symposium—Clearwater Beach, Florida USA, Apr. 29-May 2, 2007.
Class et al "Comparison of Flocked Swabs Versus Mattress Swabs and Nasal Aspirates for the Collection of Nasopharyngeal Samples", contained in U.S. Appl. No. 10/543,873 file history, titled "Swab for Collecting Biological Specimens", Triva, 23rd Annual Clinical Virology Symposium—Clearwater Beach, Florida USA, Apr. 29-May 2, 2007.
Allen et al "Comparison of a Mid-Turbinate Flocked Swab to a Nasopharyngeal Flocked Swab for Respiratory Virus Detection in Children" M-28, 24th Annual Clinical Virology Symposium and Annual Meeting of the Pan American Society for Clinical Virology, Daytona Beach, Florida, Apr. 27-30, 2008.
Christine Biggs, "Copan's Transport Medium (UTM RT) and Flocked Swab for RSV/Flu Collection" P40, contained in U.S. Appl. No. 10/543,873 file history, titled "Swab for Collecting Biological Specimens", Triva, European Society for Clinical Virology, Birmingham, UK—Sep. 3, 2008.
Vare et al "Comparison of Nylon Swabs Versus Cotton Swabs for the Diagnosis of Herpes Simplex Virus", contained in U.S. Appl. No. 10/543,873 file history, titled "Swab for Collecting Biological Specimens", Triva, ESCV 2008, Clinical Virology Annual Meeting Saariselka, Lapland, Finland, Mar. 12-15, 2008.
Waris et al "Comprison of different sampling types for the detection of rhinovirus infections using quantitative RT-PCR", contained in U.S. Appl. No. 10/543,873 file history, titled "Swab for Collecting Biological Specimens", Triva, ESCV 2008, Clinical Virology Annual Meeting Saariselka, Lapland, Finland, Mar. 12-15, 2008.
Krech et a; "Sampling of Human Papilloma Viruses and Chlamydia trachomatis: Novel Flocked Swabs Increase Detection Rates significantly", contained in U.S. Appl. No. 10/543,873 file history,

(56) References Cited

OTHER PUBLICATIONS titled "Swab for Collecting Biological Specimens", Triva, ESCV 2008, Clinical Virology Annual Meeting Saariselka, Lapland, Finland, Mar. 12-15, 2008.
Biggs et al "Evaluation . . . For the Collection of Respiratory Specimens for Cell Culture", contained in U.S. Appl. No. 10/543,873 file history, titled "Swab for Collecting Biological Specimens", Triva, Clinical Virology Symposium—CVS 2008.
Walsh et al "Comparison of Respiratory Virus Detection Rates for Infants and Toddlers by Use of Flocked Swabs, Saline Aspirates and Saline Aspirates Mixed in Universal transport Medium for Room Temperature Storage and Shipping", Journal of Clinical Microbiology, vol. 46, No. 7, pp. 2374-2376, Jul. 2008.
Daley et al "Comparison of Flocked and Rayon Swabs for Collection of Respiratory Epithelial Cells from Uninfected Volunteers and Symptomatic Patients" Journal of Clinical Microbiology, vol. 44, No. 6, pp. 2265-2267, Jun. 2006.
Chan et al :Comparison of nasopharyngeal flocked swabs and aspirates for rapid diagnosis of respiratory viruses in children Journal of Clinical Virology "Article in Press" 2008 (doi:10.1016/j.jcv.2007.12.003).
Van Horn "Comparison of the Copan ESwab System with Two Amies Agar Swab Transport Systems for Maintenance of Microorganism Viability" Journal of Clinical Microbiology, vol. 46., No. 5, pp. 1655-1658, May 2008.
Richardson et al "Lowered Sample Rejection Rate for Rapid Direct Detection of respiratory Viruses in Children by Use of a Flocked Swab and Nasopharyngeal Sampling" M25, contained in U.S. Appl. No. 10/543,873 file history, titled "Swab for Collecting Biological Specimens", Triva, 23$^{rd}$ Annual Clinical Virology Symposium—Clearwater Beach, Florida USA, Apr. 29-May 2, 2007.
Mueller et al "Recovery of Respiratory Viruses: Collected by Flocked Swabs Compared to Those Collected by Nasal Aspiration" M-34, contained in U.S. Appl. No. 10/543,873 file history, titled "Swab for Collecting Biological Specimens", Triva, Clinical Virology Symposium—CVS 2008, May 8, 2008.
DeByle et al, "Comparison of Nasopharyngeal Wash and Nasopharyngeal Flocked Swab Samples for Polymerase Chain Reaction (PCR) Detection of Viruses Causing Lower Respiratory Tract Infections in Children", 23$^{rd}$ Annual Clinical Virology Symposium—Clearwater Beach, Florida USA, Apr. 29-May 2, 2007.
Nugent et al, "Evaluation of the Physical and Diagnostic Nature of Swabs", 23$^{rd}$ Annual Clinical Virology Symposium—Clearwater Beach, Florida USA, Apr. 29-May 2, 2007.
Dalmaso et al, "Validation of the new Irradiated Nylon™ flocked QUANTISWAB™ for the quantitative recovery of micro-organisms in critical clean room environments", PDA Europe Conference and Exhibition "Best Practices in Aseptic Manufacturing", May 8-9, 2007, Milan, Italy.
Rivers et al, "Evaluation of Expanded Use of Copan Diagnostics' UTM Viral Transport Media and Eswab for the Transportation, Culture, and Nucleic Acid Detection of Trichomonas Vaginalis from Genital Samples", 23$^{rd}$ Annual Clinical Virology Symposium—Clearwater Beach, Florida USA, Apr. 29-May 2, 2007.
Castriciano et al, "Sampling Respiratory Epithelial Cells by Nasal or Nasopharyngeal Flocked Swabs", 17$^{th}$ European Congress of Clinical Microbiology and Infectious Diseases, Munich, Germany, Mar. 31-Apr. 3, 2007.
Castriciano et al, "Flocked Swabs and UTM-RT are Pre-Analytical Tools Suitable for Rapid Antigen Kits, Direct Immunofluorescence, Culture and PCR Diagnostics Assay for Viral Infections", 17$^{th}$ European Congress of Clinical Microbiology and Infectious Diseases, Munich, Germany, Mar. 31-Apr. 3, 2007.
Hjelmevoll et al, "Clinical Validation of a Real-Time Polymerase Chain Reaction Detection of Neisseria gonorrheae porA Pseudogene Versus Culture Techniques", Sexually Transmitted Diseases, May 2008, vol. 35, No. 5, pp. 517-520.
Shokoples et al, "Evaluation of Clearview → RSV and RSV Respi-Strip for the Rapid Detection of RSV from Nasopharyngeal Swabs", 23$^{rd}$ Annual Clinical Virology Symposium—Clearwater Beach, Florida USA, Apr. 29-May 2, 2007.
Lindh et al, "Orthomyxo-, paramyxo- and flavivirus infections in wild waterfowl in Finland", Virology Journal 2008, Feb. 28, 2008.
Walsh et al, "Pediatric Respiratory Infectious Disease Analysis: UTM-RT Versus Flocked Swab Nasal Collections", 23$^{rd}$ Annual Clinical Virology Symposium—Clearwater Beach, Florida USA, Apr. 29-May 2, 2007.
Starkey et al, "Respiratory Viral Recovery from Pediatric Nasopharyngeal Specimens Using Flocked Swab", Clinical Virology Symposium—CVS 2008, Apr. 27, 2008.
Schenk, "Flock Trials in Laboratory with Alternating Current", 6. Internationales Flockseminar, Sep. 8-10, 1980 pp. 135-150.
Castriciano et al, "Increased Rates of Respiratory Viral [RV] Infections Using Flocked Swabs and UTM-RT", 17$^{th}$ European Congress of Clinical Microbiology and Infectious Diseases, Munich, Germany, Mar. 31-Apr. 3, 2007.
Davidson et al, "Evaluation of Flocked Nylon Swabs (Copan Eswab) for Detection of Bacterial Pathogens by Culture and PCR", ASM 2007, American Society for Microbiology, Toronto, Canada—May 21-25, 2007.
U.S. Federal Register, Wednesday, Aug. 14, 2002, 49 CFR 171 et al., Hazardous Materials: Revision to Standards for Infectious Substances, Final Rule.
Declaration of Daniele Triva Under 37 CFR §1.132 dated Jun. 24, 2008, filed in U.S. Appl. No. 10/543,873, bearing USPTO date stamp of Jul. 3, 2008.
Body et al. "Quality Control of Microbiological Transport Systems; Approved Standard", (2003) NCCLS vol. 23, No. 34.
Grafe et al "Polymeric Nanofibers and Nanofiber Webs: A New Class of Nonwovens" to be presented at INTC 2002: International Nonwovens Technical Conference (Joint INDA-TAPPI Conference) Atlanta, GA, Sep. 24-26, 2002.
Ndaro et al. "Splitting of Islands-in-the-Sea Fibers (PA6/COPET) During Hydroentangling of Nonwovens" Journal of Engineered Fibers and Fabrics, vol. 2, Issue 4—2007, pp. 1-9.
US Patent Office, Office Actions/Communications dated Jan. 5, 2012, Dec. 20, 2011, Dec. 1, 2011, Aug. 10, 2011, in U.S. Appl. No. 10/543,873, titled "Swab for Collecting Biological Specimens", Triva.
Submissions by applicants dated Jan. 4, 2012, Dec. 16, 2011, Dec. 12, 2011 and May 27, 2011, in U.S. Appl. No. 10/543,873, titled "Swab for Collecting Biological Specimens".
US Patent Office, Office Actions/Communications dated Dec. 1, 2011 and Oct. 29, 2010, in U.S. Appl. No. 12/903,921, titled "Swab for Collecting Biological Specimens", Triva.
Submissions by applicants dated Mar. 1, 2012 and Oct. 13, 2010 , in U.S. Appl. No. 12/903,921, titled "Swab for Collecting Biological Specimens".
EP1358818(A1) Gueret (Nov. 5, 2003)—Abstract "Device for applying a product, especially cosmetics, covered with a flocking of different fibre types".
CN2554995(Y), Weng et al (Abstract) published Jun. 11, 2003"Sampler for uterine cervix".
CN1070850(A) Fuyuan (Abstract) Published Apr. 14, 1993 "constant temp. electrostatic flocking method and equipment".
CN2479505(Y) Wang (Abstract) published Feb. 27, 2002 "Microbial teting box".
DE10246379(A1) Jenner (Abstract) published Apr. 15, 2004 "Flock-coated cosmetic-applicator head has hollow basic body containing applicator holes, flock-coated surface, adhesive applicator by pressurized air".
Office Action dated Oct. 6, 2011, issued in connection with Canadian Patent Application No. 2,744,678.
Anantharamaiah et al, "Durable Nonwoven Fabrics via Fracturing Bicomponent Islands-in-the-Sea Filaments", Journal of Engineered Fibers and Fabrics, vol. 3, Issue 3, pp. 1-9, 2008.
Ofice Action dated Oct. 12, 2011, issued in connection with Canadian Patent Application No. 2,744,282.
Office Action dated Feb. 3, 2012 relating to Austra ian Patent Application No. 2010341421 of Puritan Medical Products Company, LLC . Swayam Chintamani, Patent Examination A.

(56) References Cited

OTHER PUBLICATIONS

Office Action dated Feb. 3, 2012 relating to Australian Patent Application No. 2010341422 of Puritan Medical Products Company, LLC . Swayam Chintamani, Patent Examination A.
Office Action dated Feb. 13, 2012 relating to Canadian Patent Application No. 2,744,678 of Puritan Medical Products Company, LLC.
Notice of Allowance dated Feb. 9, 2012 in Canadian Patent Application No. 2,744,282 of Puritan Medical Products Company, LLC.
Japanese Office Action dated Dec. 11, 2012 and its English translation of Jan. 15, 2013, issued in connection with Japanese Patent Application No. 2012-522817.
Cho et al, Fine Structure and Physical Properties of Polyethylene/ Poly(ethylene terephthalate) Bicomponent Fibers in High-Speed Spinning. I. Polyethylene Sheath/Poly (ethylene terephthalate) Core Fibers, Journal of Applied Polymer Science, vol. 77, pp. 2254-2266, 2000.

\* cited by examiner

COLLECTION DEVICE AND MATERIAL

The present application is a continuation of application Ser. No. 13/798,497 (issued as U.S. Pat. No. 9,274,029), filed Mar. 13, 2013 (published as US-2013-0196363 A1), which is a continuation of application Ser. No. 12/849,250 (issued as U.S. Pat. No. 8,420,385), filed Aug. 3, 2010 (published as US-2011-0262951-A1), which claims benefit of U.S. Provisional Application No. 61/326,466, filed Apr. 21, 2010, the entire contents of each of which is incorporated herein by reference.

TECHNICAL FIELD

The present disclosure describes a swab, and collection material for use therein, for collecting biological specimens.

BACKGROUND

Devices, such as swabs, for collecting biological specimens of organic material are known in the field of clinical and diagnostic analyses, which generally include a cylindrical rod or stick containing on a collection end or tip a wad of fiber material, such as rayon or a natural fiber such as cotton, with hydrophilic properties to allow rapid absorption of the quantity of specimen to be collected and tested. Stable adherence of the fiber wrapped around the end or tip of the rod or stick is generally achieved by gluing.

Collection swabs containing the collected material are often immersed in a culture media, such as in a test tube, vial, culture dish, or culture bottle, soon or immediately after collection to preserve and conserve the collected specimen during storage and/or transport to, for example, an analytical laboratory. Collection swabs and devices of the prior art are described, for example, in EP0643131 and WO2004/086979.

SUMMARY

Devices, such as swabs, and materials of the present disclosure, and methods of making same, include randomly arranged sea-island bicomponent fibers.

The present disclosure provides a swab for collecting and releasing a biological sample containing an applicator and sea-island bicomponent fibers, The swab of present disclosure contain fibers attached to an end portion of the applicator, such as by adhesive.

The present disclosure provides a method of forming the swab of the disclosure which includes adhering the bicomponent fibers to the applicator.

The present disclosure provides a method of collecting a biological sample which includes contacting the swab of the disclosure with a source of biological material such that a sample of the material is retained by the swab.

DETAILED DESCRIPTION

Figure 1:
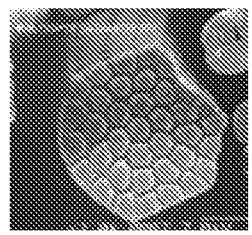
FIG. 1 provides an end view of a bicomponent fiber of PET/PET.
Figure 2:
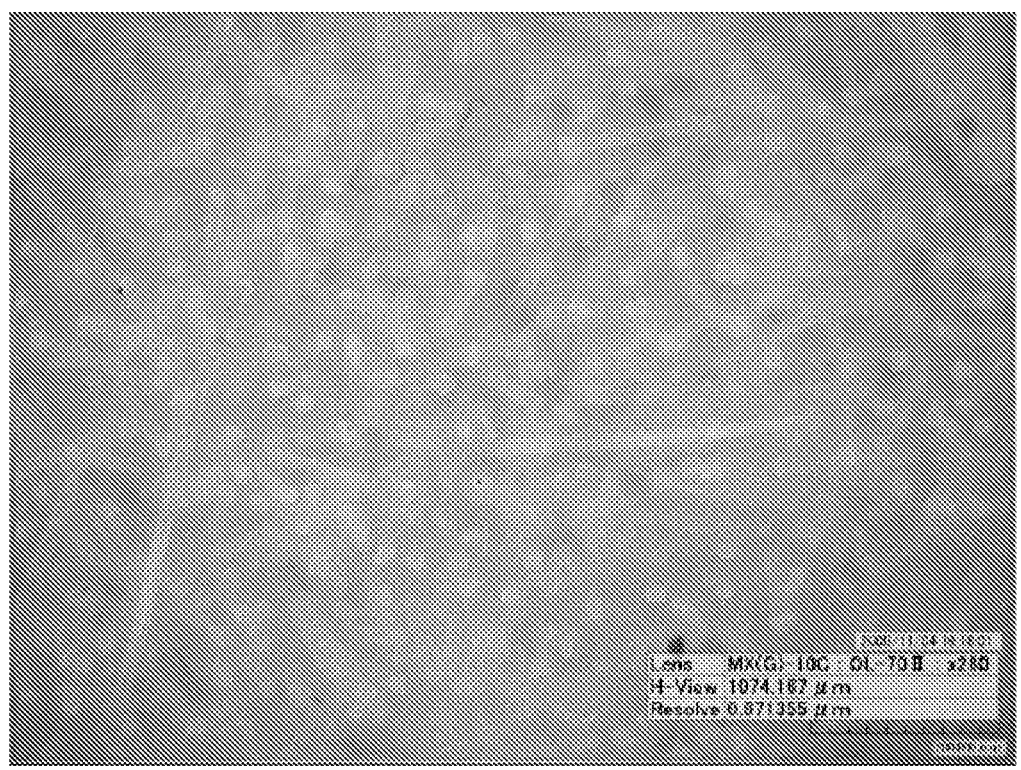
FIG. 2 is a photograph of an experimental swab stick head.

Devices, such as swabs, and materials of the present disclosure, and methods of making same, include randomly arranged sea-island bicomponent fibers.

Materials of the present disclosure may be included as a high absorbency member of medical swab devices. The "splitable" flock fiber materials of the present disclosure attached to the end of a thin "stick-like" polymeric shaft are described and contemplated herein as swabs of the present disclosure.

The materials of the disclosure may include micro- and nano-fibers, such as bicomponent sea-island materials. Segmented pie materials may also be used. Bicomponent sea-island materials and segmented pie materials are known and described, for example in Ndaro et al Journal of Engineered Fibers and Fabrics, volume 2, Issue 4, 2007 "Splitting of Islands-in-the-Sea Fibers (PA6/COPET) During Hydroentanging of Nonwovens"; and Fedorova, Nataliya "Investigation of the Utility of Islands-in-the-sea Bicomponent Fiber Technology in the SpunBond Process" Ph.D. Dissertation, North Carolina State University, Raleigh, N.C. (2006); as well as in U.S. Patent Application Publication Nos.: 20100075143 (FIBER STRUCTURE AND METHOD FOR PRODUCTION THEREOF), 20100068516 (THERMOPLASTIC FIBER WITH EXCELLENT DURABILITY AND FABRIC COMPRISING THE SAME), and 20100029158 (ISLANDS-IN-SEA TYPE COMPOSITE FIBER AND PROCESS FOR PRODUCING SAME), And WO2002042528 (A SEA-ISLAND TYPED COMPOSITE FIBER USED IN WARP KNITTING, AND A PROCESS OF PREPARING FOR THE SAME), WO2002042529 A SEA-ISLAND TYPE COMPOSITE FIBER FOR RAISED WARP KNIT FABRIC, AND A PROCESS OF PREPARING FOR THE SAME), WO2002088438 (A SEA-ISLAND TYPED CONJUGATE MULTI FILAMENT COMPRISING DOPE DYEING COMPONENT, AND A PROCESS OF PREPARING FOR THE SAME), and as are commercially available from, for example, Kolon Industry, Kumi City, Kyungbuk, Korea and generally described as ROJEL—polyester/polyester conjugated fiber yarn (sea/island) or SPECIAL TYPE OF ROJEL—polyester/nylon conjugated fiber yarn (sea/island); or Hyosung Corporation, Ulsan City, Kyungbuk, Korea and generally described as MIPAN XF—Nylon/polyester conjugated yarn (pie-wedge cross-section).

In the islands-in-sea type composite fiber of the presently described material, an easily soluble polymer is incorporated for the sea portion and preferably contains at least one polymer easily soluble in aqueous alkali solutions, such as polylactic acid, super high molecular weight polyalkyleneoxide-condensate polymers, polyethyleneglycol compound-copolymerized polyesters, and copolymerized polyesters of polyethylene glycol (PAG) compounds with 5-sodium sulfoisophthalic acid or dimethyl-5-sulfoisophthalate sodium salt (DMIS). Polyester sea materials may include alkali soluble copolymer polyester materials with polyester mainly containing polyethylene terephthalate of more than 90 mole percent as island component (such as is described, for example, in WO2002042528, the entire contents of which is incorporated herein by reference).

The islands-in-sea type bicomponent composite fiber of the present disclosure contains a sea part containing or composed of polymer of greater solubility than a plurality of island parts containing or composed of a less soluble polymer, in the cross-sectional profile of which the number of the island parts is about 10, 24, 36, 37, 64 or 240 islands per fiber, or ranges of islands per fiber between any of 10, 24, 36, 37, 64, 240 or 3000 islands per fiber.

The island component of the bicomponent composite fiber of the present disclosure may be a polyamide, such as nylon, or a polyester. Examples of the polyamide include polymers having an amide bond, such as nylon 6, nylon 66, nylon 610, and nylon 12. The polyester is not particularly limited as long as it is a polymer synthesized from dicarboxylic acid or an ester-forming derivative and diol or an ester-forming derivative thereof and can be used as the fiber. Specific examples thereof include polyethylene terephthalate, polytrimethylene terephthalate, polytetramethylene terephthalate, polycyclohexylenedimethylene terephthalate, polyethylene-2,6-naphthalene dicarboxylate, polyethylene-1,2-bis(2-chlorophenoxy)ethane-4,4'-dicarboxylate and the like. In an embodiment of the present invention, a polyethylene terephthalate or a polyester copolymer containing mainly an ethylene terephthalate unit, may be used.

The islands-in-sea type bicomponent composite fiber of the present disclosure have a linear mass density in the range of about 1-7 deniers, alternatively in the range of about 2 to 6 deniers or the range of 2 to 5.8 deniers (or 2.22 to 6.49 dtex) wherein a denier is the mass in grams per 9000 meters of fiber and dtex is the mass in grams per 10,000 meters. The diameter (Ø, in centimeters) of a bicomponent composite fiber may be estimated from the following formula, wherein ρ represents a materials density in grams per cubic centimeter:

$$\emptyset = \sqrt{\frac{4 \times 10^{-6} \cdot dtex}{\pi \rho}}$$

Estimating the fiber specific gravity as being equal to 1 (specific gravity values of common fiber polymers according to Gafe et al ("Polymeric Nanofibers and Nanofiber Webs: A New Class of Nonwovens" INTC 2002: International Nonwovens Technical Conference (Joint INDA-TAPPI Conference), Atlanta, Ga., Sep. 24-26, 2002) are as follows: 0.92 (polypropylene or PP), 1.14 (polyamide 66 or nylon or PA66) and 1.38 (polyethylene terephthalate or PET)), the diameter of bicomponent composite fiber of the present disclosure having a linear mass density in the range of 2 to 5.8 deniers would be about 16.7 μm to 28.6 μm.

The islands of the bicomponent composite fibers of the present disclosure have a mass linear density of about 0.01 to about 0.3 deniers, or about 0.05 to about 0.2 deniers, or about 0.06 to about 0.16 deniers, depending on the linear mass density of the bicomponent composite fibers of the present disclosure.

The islands-in-sea type bicomponent composite fibers of the material of the present disclosure have a length, or cut length, of about 10 to about 100 thousandths of an inch (about 254 μm to about 2,540 μm), or about 20 to about 90 thousandths of an inch, or about 20 to about 80 thousandths of an inch, or about 20 to about 70 thousandths of an inch, or about 20 to about 60 thousandths of an inch.

The islands-in-sea type bicomponent composite fibers of the material of the swabs of the present disclosure are not split. The seas of the islands-in-sea type bicomponent composite fibers of the material of the swabs of the present disclosure are not dissolved or removed from the islands of the composite fibers.

FIG. 1 is a scanning photograph of an example of a fiber of the present disclosure wherein ends of the bicomponent composite fibers is illustrated and the sea of the fiber is intact and not dissolved or removed.

The bicomponent composite fibers of the material of the present disclosure are preferably randomly arranged.

The number of fibers on a swab of the present disclosure may be evaluated by light microscope (Amscope) at 180× power with a 1 mm calibration scale (NIST) in conjunction with a video camera (Amscope 3.0 megapixel) and suitable video analysis software, such as for example, Version 3.0.12.498 Amscope video software calibrated to 180×.

A swab of the present disclosure, which includes material of the present disclosure, may be any shape adapted for collection, and optional retention, of biological samples from a host directly or already collected biological fluid or sample. Shapes and sizes of such devices are known in the art. The swab of the present disclosure is constructed of materials known in the art, such as acrylonitrile-butadiene-styrene (ABS). The swab of the present disclosure is such that the material of the present disclosure may be attached to the applicator of the swab through an adhesive during a flocking technique known in the art.

An applicator of the swab of the present disclosure may be a rod or rod-like thermoplastic substrate wherein one end is coated, partially, substantially or completely, with an adhesive to anchor or hold fibers of the present disclosure to the substrate in an initial arrangement generally perpendicular to the substrate and generally parallel to adjacent fibers to thereby create, for example, a bristle or bristly end on the substrate.

In a method of making devices according to the present disclosure, individual, loose or connected substrate, such as applicator shafts, sticks or rods have adhesive applied by at least one adhesive applicator container, block, head, nozzle, or roller by, for example, spraying, dipping, rolling, printing or a combination thereof, optionally in a metered fashion, under pressure or by gravity, and in a manner which may or may not include any combination of linear and/or rotational, such as by axial rotation or spinning, of the adhesive applicator relative to the applicator.

In the flocking technique of the present disclosure, an electric field of alternating or direct current is applied to the fibers in a manner know in the art to organize and transport charged fibers to opposite charged adhesive-covered substrate such that the fibers are held in place by the tackiness or adhesive strength of the adhesive, only in areas where the adhesive has been applied to produce flock fiber tipped applicators, or swabs of the disclosure. The technique may include movement of the substrate, linearly and/or rotationally, such as by axial rotation or spinning, at any time or throughout the process of applying fibers to the adhesive. Where further curing of the adhesive, such as by light or heat, is required, the flock fiber tipped applicator swab may be treated with light and/or heat so as to cure the adhesive.

Swabs of the disclosure may contain approximately $10^4$ to approximately $10^{10}$, or approximately $10^4$ to approximately $10^9$, or approximately $10^4$ to approximately $10^8$, or approximately $10^4$ to approximately $10^7$, or approximately $10^4$ to approximately $10^6$, or approximately $10^4$ to approximately $10^5$, flock fibers per substrate.

The adhesive of the present disclosure is not particularly limited and general and photo or heat cured acrylic-based, polyurethane-based, polyamide-based, polyester-based, vinyl-based and/or two-part epoxy adhesives may be used. Silicones, cyanoacrylates, polyurethanes and/or latex adhesives may be used. Polyurethane adhesive are generally known and available, such as from K&W Adhesive Products.

The swabs of the present disclosure are adapted or designed for collection of, for example, biological samples from oral, nasal, ocular, rectal, urethral, or vaginal orifices of a mammal, such as a human, or patient.

The swabs may be used and is designed for collection of a biological specimen by contact with the fibers of the device such that the device may collect, for example, about 35 to about 200 μl, such as 40, 50, 60, 70, 80, 90, 100, 120, 130, 140, 150, 160, 170, 180 or 190 μl, without causing damage or substantial discomfort to the patient during specimen collection.

The swabs of the present disclosure is useful for and in a method of collecting biological specimens. A swab of the present disclosure is of the type containing a rod terminating with a tip covered in the fibers described herein to allow absorption of said specimens, wherein the fibers cover or substantially cover the tip in the form of a layer applied by means of flocking.

The present disclosure further provides a method of collecting a biological sample which includes contacting a swab as described herein with a source of biological material such that a sample of the material is retained by the swab.

The swabs of the disclosure may be provided, for example, as a component part of a collection, transport, culture and/or transport kit or device wherein additional specimen handling containers and/or devices are included and the swab of the present disclosure is specially adapted to be integrated with such other container and/or devices to assure, for example, specimen retention, integrity and/or sterility.

The present disclosure provides a swab for collecting and releasing a biological sample containing sea-island bicomponent fibers. The swabs may further contain bicomponent fibers which are composed of a first polyester sea material and a second polyester island material; the first polyester may have a lower melting point than the second polyester and/or the first polyester may have a greater solubility in alkaline solution than the second polyester. The alkaline solution may more specifically be a sodium hydroxide solution—the sodium hydroxide solution may contain about 5% to about 50% by weight sodium hydroxide in water, or alternatively about 10% by weight sodium hydroxide in water. The alkaline solution wherein the first polyester sea material is more soluble than the second polyester sea material may be a heated alkaline solution —the heated alkaline solution alternatively having a temperature of about 170° F. to about 190° F., such as about 180° F.

The present disclosure provides a swab, wherein material described herein is attached to an end portion of an applicator stick or rod. The material may be adhered to the end of the applicator with an adhesive, and the adhesive may be a photocurable acrylic adhesive or a polyurethane adhesive.

The bicomponent fibers of the present disclosure may be composed of a polyethylene terephthalate sea material and a polyamide island material.

The bicomponent fibers of the present disclosure may be composed of or contain 10-3000 island parts per fiber, 10-240 island parts per fiber, 10-64 island parts per fiber, 10-37 island parts per fiber, 10-36 island parts per fiber, 10-24 island parts per fiber, and/or 24-36 island parts per fiber.

The present disclosure provides the fibrous material of the swab described herein. The fibrous material may be incorporated separately as a part of a device other than a swab, such as a filter or cleaning pad or brush.

The present disclosure provides a method of forming a swab of the disclosure involving adhering the bicomponent fibers to an applicator, such as a rod or stick, wherein the sea component of the fiber is not removed.

The following examples further illustrate the materials and methods of the disclosure without limiting same.

EXAMPLE 1

Swabs

A quantity of (about 30 or so) experimental medical swabs were prepared from ABS plastic "sticks" of Puritan Medical Products (Guilford, Me.) with 0.5 mm long (0.020", nominal length, as determined by a Flock-In-Spect flock fiber length optical measurement instrument) Nylon/PET sea/island type flock fiber. Two adhesive systems were employed in these experimental fabrications; the polyurethane rubber (K&W polyurethane adhesive—MECFLOCK L876/1, MEDCODUR H5530 two part polyurethane adhesive, mixed 85 grams L876/1 resin and 15 grams H5530 hardener—product of Kissel and Wolf; cured 3 hours at 110° C. or else cured 16 hours at 80° C.). and a UV photo-curable adhesive from Puritan Medical Products.

The following materials and instruments were used in fabrication: ABS (plastic) swab sticks (supplied by Puritan); Maag Flockmaschinen Motion (flock activity) Tester SPG 1000; K & W adhesive in a shallow aluminum dish (adhesive depth about 1 cm); photo-curable adhesive in light-blocked packet; flock screen sifter; and a supply of Nylon/PET 0.5 mm long Flock fibers The experimental swabs were fabricated as follows. The flock activity tester's 4" diameter aluminum base plate is covered (by sifting) with about 2 grams of loose flock. This sample of loose flock was mounted on to the bottom electrode pedestal of the Flock Activity Tester. The end of the swab sticks were perpendicularly dipped into the fluid K & W adhesive to a depth of about 1 cm and slowly removed to produce end-coated swab-sticks. Some swab samples were made using photo-curable adhesive. Water-based acrylic (F1059B Lubrizol Corp.) flock adhesive and other water based adhesives could be used. A 3.5 KV/cm strength was applied to the DC electrodes of the Flock Activity Tester (upflocking machine). This causes the flock fibers to align themselves and actively move to the top electrode. As this flock is being propelled from the bottom to the top electrode, the adhesive coated tip plastic swab-stick is then placed in the "flock fiber cloud" about 1 cm from the bottom electrode (source of the activated flock fibers). While in the "flock fiber cloud", the swab-stick was slowly rotated by rolling the stick held in gripping fingers.

Flock fibers fully adhered to the saturate at the (adhesive wet) end of the swab-stick after about a 2 to 5 second flock field immersion time. The swab adhesive was subsequently cured.

The average amount of adhesive and the average amount of flock applied to the ABS base (sticks) were determined by weight with the following results: average weight of "Bare" ABS sticks: 0.5644+/−0.00426 grams; average weight of K & W Adhesive on "Sticks" before flocking: 0.0046 grams; and average weight of PET/Nylon Flock on "Sticks": 0.0135 grams. With an average of 0.0135 grams of sea/island flock fiber on each "stick" this translates to approximately 1.2 ×$10^5$ flock fibers per "stick".

The water "pick-up" capabilities of the flocked medical swabs was determined by a procedure whereby a number of swab and "stick" materials were first weighed (dry). Then this same series of flocked swabs and "sticks" were immersed in room temperature (23° C.) water (tips only) for 5 seconds and then reweighed.

The percent water pick-ups of the various swab configurations were then compared. The results demonstrate that the "bare" ABS swab sticks pick-up or capture little or no water. The polyurethane adhesive coated (tip only) swabs picked up or captures a little water indicating that the adhesive is a more wettable surface that the "bare" ABS. The flocked fiber swab picked up or captured a measurable amount of water (8.95%).

Several fiber material types (of sea/island fiber) have been evaluated. The nylon/PET (Kolon) and PET/PET (Kolon-Rojel) fibers appear useful in the fiber flocked medical swab application of the present disclosure. While 0.5 mm long nylon/PET flock fiber were initially investigated, fibers of various sizes may be used and are contemplated.

The following two flock adhesives have been investigated: the two-package polyurethane (clear rubbery) and the photo-curable (clear film plastic) systems. Other adhesives are contemplated.

All literature and publications referred to and described herein are incorporated herein in their entirety.

We claim:

1. A swab constructed to collect and release a biological sample comprising a flock fiber tipped applicator wherein the flock fibers are sea-island bicomponent fibers attached to an end portion of said applicator with an adhesive selected from the group consisting of a photocurable acrylic adhesive and a polyurethane adhesive, the bicomponent fibers being structurally stable in water and the sea component of the bicomponent flock fibers being intact, and wherein the bicomponent fibers comprise 10-3000 island parts per fiber.

2. The swab of claim 1 wherein said bicomponent fibers comprise a first polyester sea material and a second polyester island material.

3. The swab of claim 2 wherein said first polyester has a lower melting point than said second polyester.

4. The swab of claim 2 wherein said first polyester has a greater solubility in alkaline solution than said second polyester.

5. The swab of claim 4 wherein the first polyester has a greater solubility in alkaline solution of sodium hydroxide, as compared to the second polyester.

6. The swab of claim 5 wherein the first polyester has greater solubility in an alkaline solution of sodium hydroxide solution containing about 5% to about 50% by weight sodium hydroxide in water, as compared to the second polyester.

7. The swab of claim 6 wherein the first polyester has greater solubility in an alkaline solution of about 10% by weight sodium hydroxide in water, as compared to the second polyester.

8. The swab of claim 4 wherein the first polyester has greater solubility in a heated alkaline solution as compared to the second polyester.

9. The swab of claim 8 wherein the first polyester has greater solubility in an alkaline solution heated to a temperature of about 170° F. to about 190° F. as compared to the second polyester.

10. The swab of claim 1 wherein said bicomponent fibers comprise a polyethylene terephthalate sea material and a polyamide island material.

11. The swab of claim 1 wherein said fibers comprise 10-240 island parts per fiber.

12. The swab of claim 1 wherein said fibers comprise 10-64 island parts per fiber.

13. The swab of claim 1 wherein said fibers comprise 10-37 island parts per fiber.

14. The swab of claim 1 wherein said fibers comprise 10-36 island parts per fiber.

15. The swab of claim 1 wherein said fibers comprise 10-24 island parts per fiber.

16. The swab of claim 1 wherein said fibers comprise 24-36 island parts per fiber.

17. A method of forming the swab of claim 1 comprising adhering the bicomponent fibers to said applicator.

18. A method of collecting a biological sample comprising contacting the swab of claim 1 with a source of biological material such that a sample of the material is retained by the swab.

* * * * *